United States Patent
Cisko, Jr.

(10) Patent No.: US 6,830,565 B2
(45) Date of Patent: Dec. 14, 2004

(54) ADHESIVE FACEPLATE FOR OSTOMY APPLIANCE HAVING MIRRORED RELEASE SHEET

(75) Inventor: George J. Cisko, Jr., Spring Grove, IL (US)

(73) Assignee: Hollister Incorporated, Libertyville, IL (US)

( * ) Notice: Subject to any disclaimer, the term of this patent is extended or adjusted under 35 U.S.C. 154(b) by 251 days.

(21) Appl. No.: 10/133,875

(22) Filed: Apr. 26, 2002

(65) Prior Publication Data

US 2003/0204174 A1 Oct. 30, 2003

Related U.S. Application Data

(60) Provisional application No. 60/288,860, filed on May 4, 2001.

(51) Int. Cl.[7] .................................................. A61M 1/00
(52) U.S. Cl. ....................................................... 604/336
(58) Field of Search ................................ 604/277, 327, 604/332–345, 385.05, 543; 602/41–79

(56) References Cited

U.S. PATENT DOCUMENTS

| | | | | |
|---|---|---|---|---|
| 2,733,110 A | * | 1/1956 | Berner et al. .................. 108/9 |
| 3,148,461 A | * | 9/1964 | Johnson ....................... 434/185 |
| 4,205,678 A | * | 6/1980 | Adair .......................... 604/343 |
| 4,257,680 A | * | 3/1981 | Baczkowski ................. 359/879 |
| 4,534,354 A | * | 8/1985 | Bonner et al. ............... 607/108 |
| 4,686,355 A | * | 8/1987 | Lay ............................. 219/385 |
| 4,726,354 A | * | 2/1988 | Fujita .......................... 600/32 |
| 4,745,916 A | * | 5/1988 | Seber .......................... 128/858 |
| 4,925,285 A | * | 5/1990 | Dowdell et al. ............ 359/860 |
| 4,995,410 A | * | 2/1991 | Lash ........................... 134/113 |
| 5,202,168 A | | 4/1993 | Turner et al. |
| 5,405,671 A | * | 4/1995 | Kamin et al. ................. 428/69 |
| 5,531,670 A | * | 7/1996 | Westby et al. ................ 602/41 |
| 5,662,624 A | * | 9/1997 | Sundstrom et al. ......... 604/291 |
| 5,704,905 A | * | 1/1998 | Jensen et al. ................. 602/58 |
| 6,191,339 B1 | * | 2/2001 | Gueret ......................... 602/58 |
| 6,563,012 B2 | * | 5/2003 | Hill .............................. 602/41 |
| 6,692,773 B2 | * | 2/2004 | Burrell et al. .............. 424/618 |
| 2001/0047144 A1 | * | 11/2001 | Tillotson et al. ............. 602/41 |
| 2003/0153883 A1 | * | 8/2003 | Hansen et al. ............. 604/337 |
| 2003/0167029 A1 | * | 9/2003 | Augustine ................... 602/42 |

FOREIGN PATENT DOCUMENTS

DE 199 04 315 8/2000
GB 2 199 501 A * 7/1988 ........... A61F/13/00

* cited by examiner

Primary Examiner—John J. Calvert
Assistant Examiner—Michael Bogart
(74) Attorney, Agent, or Firm—Marshall, Gerstein & Borun LLP

(57) ABSTRACT

An adhesive wafer for use as the faceplate of an ostomy appliance is disclosed. The wafer includes an adhesive layer of hydrocolloid-containing material having first and second surfaces, a flexible backing layer covering the first surface, and a removable release sheet extending over the second surface. The release sheet has at least a portion of its outer surface mirrored to reflect images during application of the wafer to the peristomal skin surfaces of an ostomate.

7 Claims, 1 Drawing Sheet

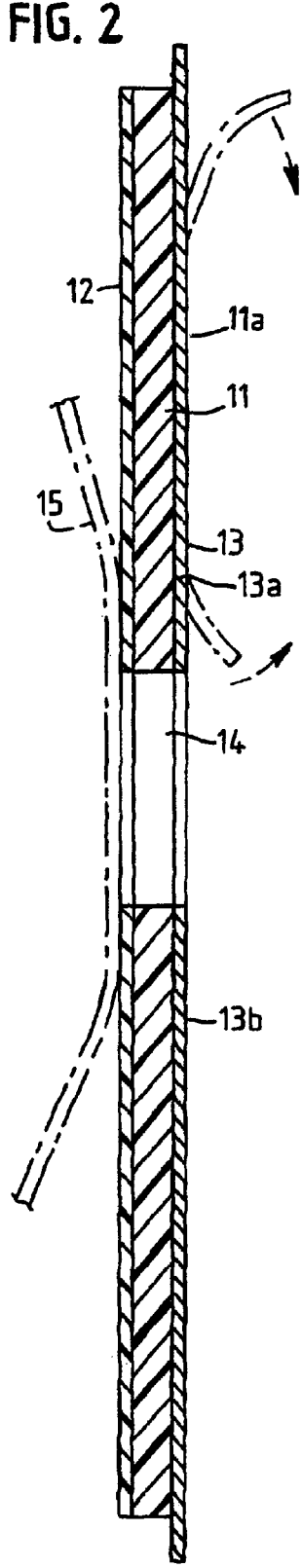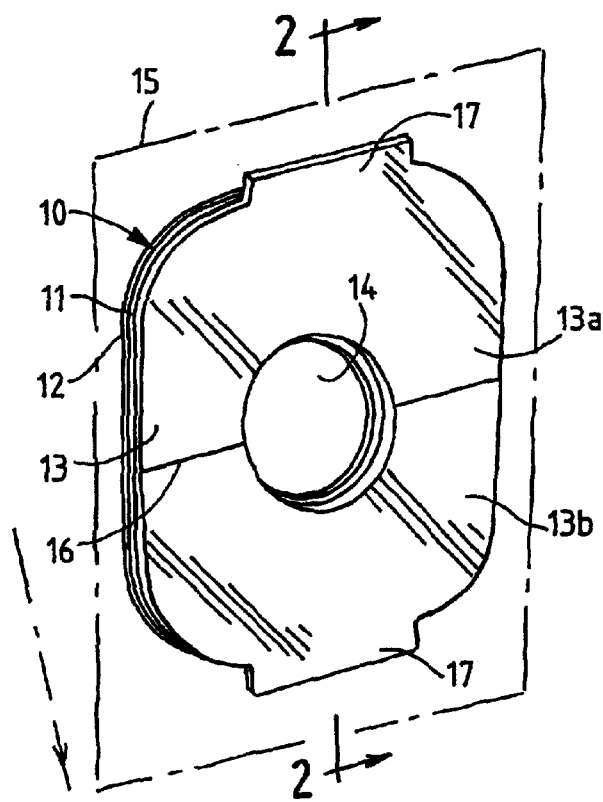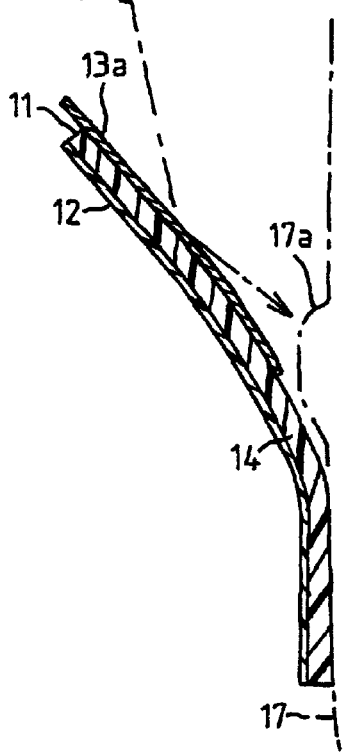

ADHESIVE FACEPLATE FOR OSTOMY APPLIANCE HAVING MIRRORED RELEASE SHEET

REFERENCE TO RELATED APPLICATIONS

This application is entitled to priority to U.S. Provisional Application No. 60/288,860, filed May 4, 2004, as to all subject matter commonly disclosed therein.

BACKGROUND AND SUMMARY

Adhesive wafers, especially those of the type commonly used as faceplates for ostomy appliances, are often difficult for ostomates (and caregivers) to apply. At the time of application, such a faceplate usually has its opening sized, and often shaped, to match a patient's stoma, but the job of securing the faceplate to peristomal skin surfaces, with the stoma properly located in the opening, can be a challenging task.

To help in orienting and positioning such a faceplate, ostomates sometimes use hand-held mirrors to obtain a clearer view of the target area. That only complicates the problem, since holding and directing an ostomy appliance generally requires two hands. If one hand is used to hold a mirror, then the user faces the even more difficult task of trying to direct and apply the ostomy faceplate with only a single hand.

The problem is not limited to the application of ostomy faceplates. Wound dressings for decubitus ulcers must often be applied to areas of the body not easily viewed by patients. Such an adhesive dressing commonly has a specific area that must be positioned directly over a wound as the dressing is applied, an accomplishment that may exceed the ability of many patients, such as an elderly patient of limited dexterity.

This invention is therefore directed towards reducing the aforementioned problems by allowing a user, either a patient or a caregiver, to use both hands in holding, directing and applying an adhesive wafer while having a clear reflected image of the target area. More specifically, the invention takes the form of an adhesive wafer for use as a faceplate of an ostomy appliance or a wound dressing, in which the wafer has an adhesive layer of a hydrocolloid-containing skin barrier material and in which the skin-engagable surface of the adhesive layer is covered by a removable release sheet having a mirrored outer surface. Ideally, such a release sheet has two or more divisible and individually removable sections. One or more pull tabs are provided along the edges of the release sheet to facilitate removable of said sheet, or the sections thereof, at the time of application of such a wafer.

DRAWINGS

FIG. 1 is a prospective view of an adhesive wafer embodying this invention.

FIG. 2 is an enlarged sectional view taken along line 2—2 of FIG. 1.

FIG. 3 is a sectional view illustrating application of such a dressing to a patient.

DETAILED DESCRIPTION

In FIG. 1, the numeral 10 generally designates an adhesive wafer consisting essentially of three layers: a core layer 11 of adhesive material covered on one side by a backing layer 12 and on its opposite side by a removable release sheet 13. In the embodiment illustrated, the wafer constitutes the faceplate of an ostomy appliance and has a centrally-located stoma-receiving opening 14 extending through all three layers. Backing layer 12 is permanently attached about the periphery of the opening to an ostomy pouch 15, a portion of which is shown in phantom in FIGS. 1 and 2. The permanently-connected faceplate and pouch constitute what is commonly referred to as a one-piece appliance but, alternatively, the faceplate might be one component of a two-piece appliance, with the faceplate and pouch being separable and detachably connected together by adhesive or mechanical coupling means.

While the wafer shown in the drawings constitutes an ostomy faceplate, it is to be understood that it might alternatively take the form of a wound dressing.

The adhesive layer 11 is preferably composed of a moisture-absorbing and moisture-swellable skin barrier material having a continuous phase composed of one or more tacky elastomers and a discontinuous phase consisting essentially of one or more hydrocolloids dispersed throughout the adhesive layer. Typical hydrocolloids are pectin, gelatin and sodium or calcium carboxymethylcellulose, but other hydrocolloids such as karaya may be used. If desired, superabsorbents may also be included in the barrier formulation. The continuous elastomeric phase may be composed of a tacky, deformable elastomeric material such as polyisobutylene and/or a block copolymer such as styrene-isoprene-styrene copolymer of the type described in U.S. Pat. Nos. 4,738,257 and 4,231,369. Tackifiers, plasticizers, extenders and stabilizers may be included, all as well known in the art. One example of a barrier composition suitable for use for adhesive layer 11 is disclosed in aforementioned U.S. Pat. No. 4,738,257, but other hydrocolloid-containing compositions known for use for ostomy faceplates and wound dressings may be used.

Backing layer 12 may be unitary (as shown) or may itself consist of multiple layers. It must be flexible and may be stretchable and contractable for purposes of anatomical conformity. It should also be heat-sealable, especially where the wafer is to function as a ostomy faceplate (as shown). The backing layer may be formed of a thin film of polyurethane, polyethylene, or other suitable thermoplastic material. Alternatively, it may be a soft, flexible thermoplastic foam of closed, semi-open, or fully-open cell construction. Polyurethane or polyethylene foams are believed to be suitable, but other thermoplastic foams having similar properties may be used. Particularly effective results for purposes of an ostomy appliance are obtained where the backing layer 12 is composed of a soft, porous, non-woven fabric of thermoplastic fibers such as, for example, a non-woven fabric of spun-bonded polyethylene fibers.

Release sheet 13 serves as a removable cover to protect the surface 11a of the adhesive layer 11 prior to application to a patient. It should be flexible but preferably non-stretchable. A paper having a siliconized surface in contact with adhesive surface 11a may be used. Alternatively, release sheet 13 may be composed of a flexible plastic film or even a metal foil. In any event, an essential feature of release sheet 13 is that its outwardly-facing surface is mirrored and image-reflecting. The reflectiveness of sheet 13 may be achieved by providing the paper or plastic film with a reflective metallic coating. Such sheet materials are known and commercially available. Two such materials are available from 3M Medical Specialties, Minneapolis, Minn. under the designations 3M Visible Mirror film MSX-5002 and 3M Colored Mirror film MSX-5003, and are reflective without having pigments, dyes or metals, but other materials having image-reflecting properties may be used. Whatever reflective material is selected, its surface contacting adhesive layer 11 should be formulated or coated to allow the release sheet to be peeled away as indicted in broken lines in FIG. 2.

Release sheet 13 may be unitary or may have a plurality of divisible and individually removable sections. It may also cover only a portion of the adhesive layer, with the remainder of the adhesive layer being covered by a conventional non-reflective release sheet or, alternatively, the respective layer may be in the form of a relatively small patch affixed to the surface of a standard non-reflective release sheet. In the embodiment shown, the reflective release sheet has separately removable upper and lower sections 13a and 13b, respectively, meeting along midline 16. Each section may have at least one tab portion 17 that projects outwardly beyond the periphery adhesive layer 11 to facilitate removal of such section from adhesive surface 11a of adhesive layer 11.

It is to be noted that the wafer 10 should be supplied to a user with at least its reflective bodyside surface in planar condition. The wafer may therefore be held and used as a mirror for visually examining a stoma or wound site in preparation for wafer application. Following such inspection, lower section 13b may be peeled away and the exposed adhesive surface applied to the skin beneath stoma 17a as illustrated in FIG. 2. With the upper section 13a still in place, the user may continue to inspect the stomal area by viewing that area along the sight line 18 represented in FIG. 3. After determining that the wafer is properly aligned with the stoma, the remaining section 13a of the release sheet is then removed and the adhesive attachment of the wafer is completed.

While adhesive layer 11 is preferably composed of a hydrocolloid-containing adhesive material, other adhesives having similar properties, such as adhesive hydrogel materials, might also be used. In general, hypo-allergenic adhesives suitable for contact with the skin, as commonly used with wound dressings, are believed suitable.

What is claimed is:

1. An adhesive wafer for use as a faceplate of an ostomy appliance or as a wound dressing, said wafer comprising an adhesive layer of a hydrocolloid-containing skin barrier material having first and second surfaces, a flexible backing layer extending over first surface, and a removable release sheet extending over said second surface, said release sheet having a mirrored image-reflecting outer surface.

2. The wafer of claim 1 in which said release sheet has a plurality of divisible and individually removable sections.

3. The wafer of claim 1 or 2 in which said release sheet, or each section thereof, is provided with a pull tab extending outwardly beyond said adhesive layer for use in manually peeling said release sheet, or each section thereof from said adhesive layer.

4. The structure of claim 1 in which said wafer is a faceplate for an ostomy appliance, said backing layer including means for connecting said faceplate to an ostomy pouch.

5. The structure of claim 4 in which an ostomy pouch is connected to said backing layer of said wafer.

6. An adhesive wafer for use as an ostomy faceplate or wound dressing comprising an adhesive layer of a hydrocolloid-containing skin barrier material having first and second surfaces, a flexible backing layer extending over said first surface, and a removable release sheet extending over said second surface, said release sheet having at least a portion thereof provided with a mirrored image-reflecting outer surface.

7. The wafer of claim 6 in which said reflective portion of said release sheet comprises a reflective patch affixed to the outer surface of said release sheet.

* * * * *